United States Patent
Belzidsky

[19]

[11] Patent Number: 6,149,690
[45] Date of Patent: Nov. 21, 2000

[54] PROSTHESIS SUSPENSION SLEEVE

[76] Inventor: Hugo Belzidsky, 373 S. Coast Blvd., Unit 6, La Jolla, Calif. 92037

[21] Appl. No.: 09/260,789

[22] Filed: Mar. 2, 1999

[51] Int. Cl.$^7$ ........................................................ A61F 2/78
[52] U.S. Cl. .................................. 623/32; 623/33; 602/33
[58] Field of Search ..................... 623/32–36; 602/62–63

[56] References Cited

U.S. PATENT DOCUMENTS

| | | |
|---|---|---|
| 4,479,272 | 10/1984 | Beldzisky . |
| 4,634,446 | 1/1987 | Kristinsson . |
| 4,822,371 | 4/1989 | Jolly et al. . |
| 4,923,474 | 5/1990 | Klasson et al. . |
| 5,152,800 | 10/1992 | Rothschild et al. . |
| 5,571,208 | 11/1996 | Caspers ...................................... 623/32 |
| 5,593,454 | 1/1997 | Helmy . |
| 5,769,809 | 6/1998 | Witzel . |

*Primary Examiner*—Bruce Snow
*Attorney, Agent, or Firm*—Haugen Law Firm PLLP

[57] ABSTRACT

A flexible urethane suspension sleeve for use in attaching a below the knee prosthesis to the remaining portion of the patient's limb. The sleeve has a generally tubular shape and includes a preflexed portion. A reinforced intermediate portion provides for abrasion resistance in the portion of the sleeve covering the socket "ears" and is disposed intermediate first and second reinforced end portions having different elasticities. A pair of non-compressive portions are disposed intermediate the reinforced intermediate portion and the reinforced end portions and provide for a non-compressive suction adhesion to the thigh of the user and the prosthesis.

11 Claims, 2 Drawing Sheets

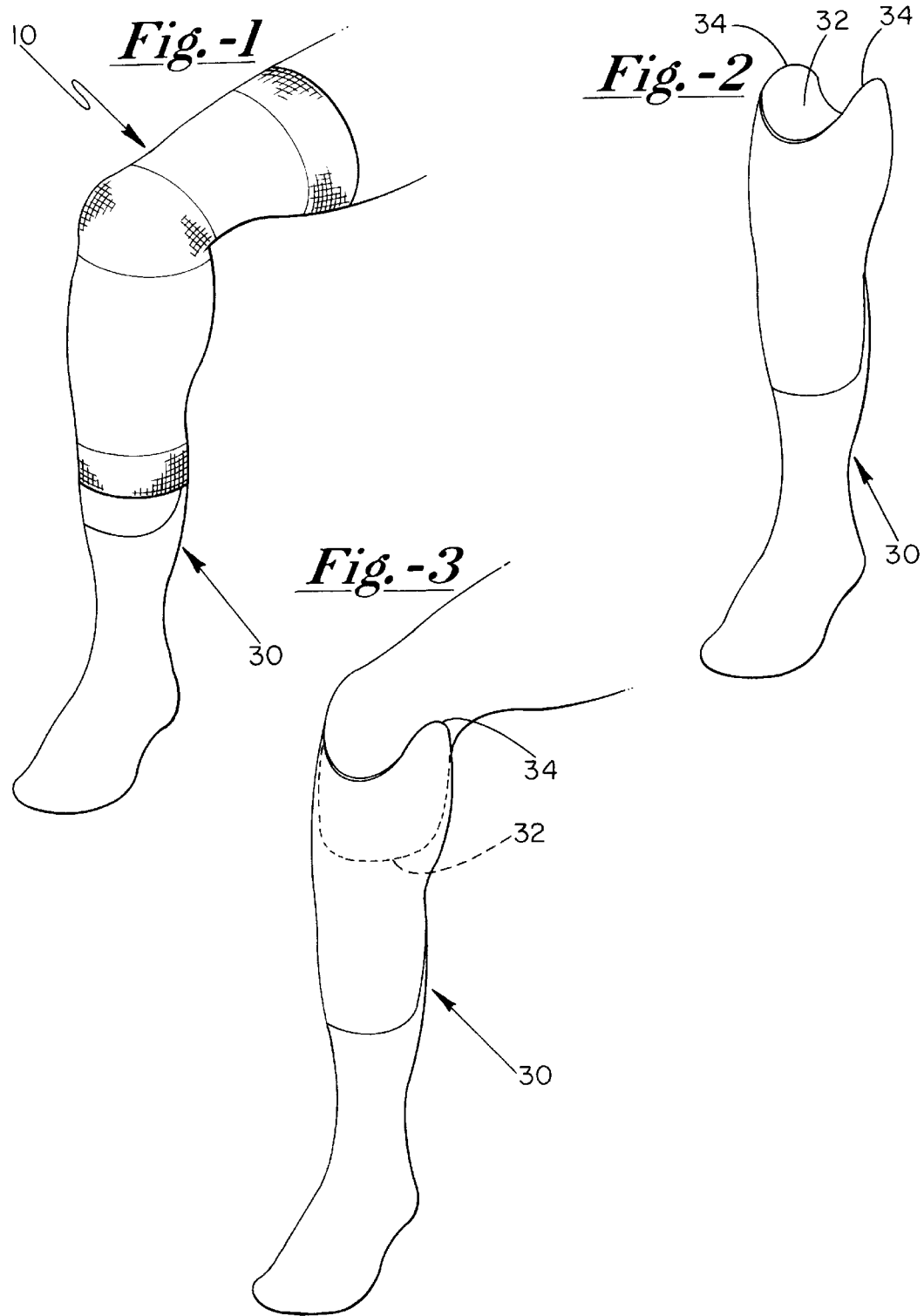

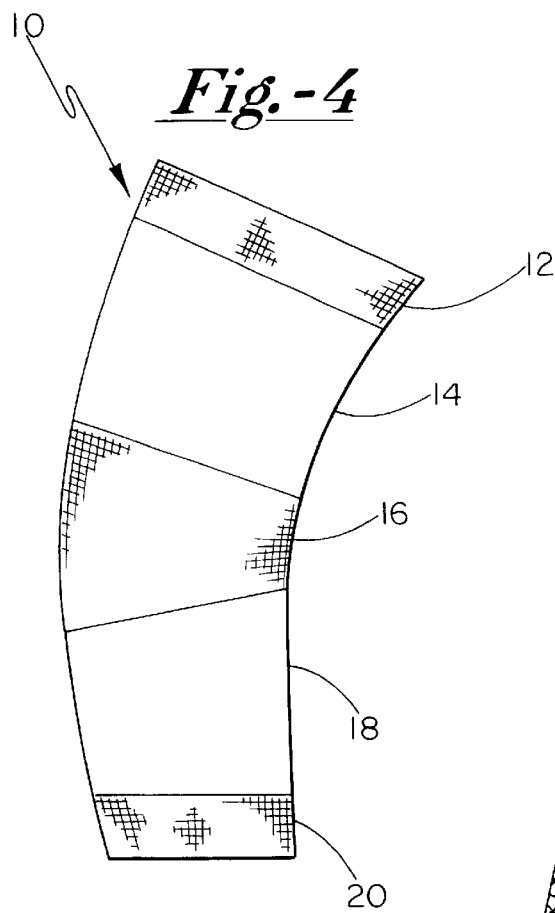
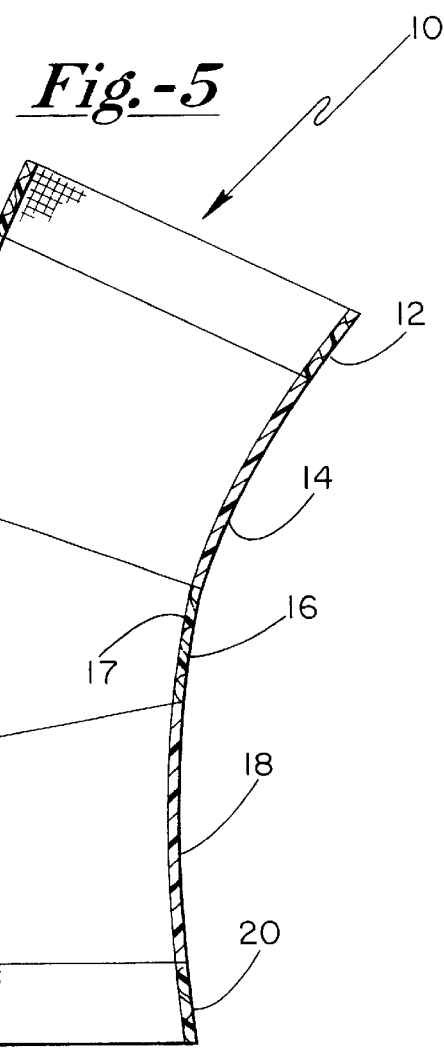

PROSTHESIS SUSPENSION SLEEVE

BACKGROUND OF THE INVENTION

1. Field of the Invention

The present invention relates to a prosthesis suspension sleeve for use in attaching a below the knee prosthesis to the remaining portion of the patient's limb and more particularly pertains to a flexible, non-compressive urethane sleeve having integrally formed reinforced portions which provide for varying degrees of axial and circumferential stretching. The reinforced portions provide mechanical strength and resistance to tearing.

2. Description of the Prior Art

The general problem of attaching or suspending a below knee prosthesis to the remaining portion of a patient's limb has been addressed in the prior art. Various means and apparatus have been developed with the goal of providing a secure attachment that provides the amputee the ability to conduct his affairs without fear of losing his prosthesis during normal or strenuous activities. Mechanical means such as suspension belts and thigh lacers suffer from the disadvantage of being compressive about the thigh and of constricting the blood circulation in the thigh. Additionally, these devices do not solve the problem of pistoning, wherein the residual limb moves within the socket of the prosthesis in response to forces exerted upon the prosthesis. Pistoning further promotes tissue and skin problems including but not limited to irritation, lesions, and abundant perspiration.

In an attempt to solve these problems, sleeves made of elastic materials were developed. One such sleeve is disclosed in U.S. Pat. No. 5,593,454 to Helmy which discloses a sleeve having a reinforcing web formed throughout the sleeve. The web may be formed in either of two different weave patterns for controlling the stretch parameters of the sleeve. The sleeve itself has a barrel shape which provides smaller openings at the ends of the sleeve than would a cylinder.

A reinforced elastic sleeve is also disclosed in U.S. Pat. No. 4,822,371 to Jolly et al. This sleeve includes an internal cylindrical like panel which has a fabric surface with a low coefficient of friction. It is claimed that the panel serves to decrease irritation to the wearer and to improve the durability of the sleeve.

Another example of a prosthesis sleeve is disclosed in U.S. Pat. No. 4,479,272 to Beldzisky. A retaining sheath is disclosed which is open at both ends and includes an upper elastic retention portion, a lower elastic retention portion, and an intermediate articulation portion. The two end portions are axially non-stretchable, but are radially elastically stretchable. The middle portion is stretchable both axially and circumferentially.

In U.S. Pat. No. 5,769,809 a limb protector apparatus is disclosed which provides for progressively variable capacity for resilient stretching along the length of a tubular member.

All of the above-identified apparatus provide for attachment of the prosthesis to the limb by means of compression or constriction of the thigh. As is well known, many amputees have circulatory problems which are exacerbated by the apparatus of the prior art. A tourniquet effect restricts the flow of blood in the residual member, leading to discomfort and other complications.

Another method of suspending or attaching a below knee prosthesis is disclosed in U.S. Pat. No. 4,923,474 to Klasson et al. A sleeve member having a frusto-conical shape with a truncated end encloses an amputation stump. A coupling means is formed at the distal end of the sleeve for attachment to a prosthesis or other appliance.

While this type of apparatus provides for suitable adhesion of the inside of the socket liner to the skin of the stump, forces acting upon the distal coupling means cause stretching of the skin. This stretching of the skin promotes the aforementioned skin and tissue problems associated with pistoning.

It would therefore be desirable to provide a durable prosthesis suspension sleeve for use in attaching a below the knee prosthesis to the remaining portion of the patient's limb which can be used either alone or in combination with a sleeve attachable to a prosthesis and that eliminates the problem of pistoning and which non-compressively adheres to the prosthesis and to the limb.

SUMMARY OF THE INVENTION

Accordingly, it is a primary object of the present invention to provide a flexible urethane prosthesis suspension sleeve capable of non-compressive adhesion to both the limb and the prosthesis.

It is a further object of applicant's invention to provide a sleeve having integrally formed reinforced portions which provide for mechanical strength and resistance to tearing.

It is a still further object of applicant's invention to provide a sleeve having integrally formed reinforced portions having varying degrees of axial and circumferential stretching.

It is a further object of applicant's invention to provide a sleeve having a reinforced portion disposed intermediate end portions of the sleeve.

It is a further object of the applicant's invention to provide a sleeve having reinforced end portions having different stretch parameters.

Various of the foregoing objects, advantages and distinctions of the invention are particularly obtained in a flexible urethane sleeve of generally tubular shape having a first reinforced end portion stretchable circumferentially, an opposed second reinforced end portion of limited circumferential stretchability or elasticity, a reinforced intermediate portion disposed between the first reinforced end portion and the second reinforced end portion and stretchable both circumferentially and axially, a first non-compressive portion disposed intermediate the reinforced intermediate portion and the first reinforced end portion, and a second non-compressive portion disposed intermediate the reinforced intermediate portion and the second reinforced end portion. The first and second reinforced end portions and the reinforced intermediate portion contain textile reinforcements, the reinforcement providing mechanical strength against tearing but not affecting the compressibility of the urethane.

The sleeve has a generally truncated conical shape wherein the second reinforced end portion has a smaller diameter than the first reinforced end portion. Additionally, the sleeve is preflexed as further described hereinafter.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the prosthesis suspension sleeve shown in use.

FIG. 2 is a perspective view of a typical below the knee prosthesis.

FIG. 3 is a perspective view showing the below the knee stump positioned within the socket of the prosthesis.

FIG. 4 is a side elevation view of the sleeve of the present invention.

FIG. 5 is a cross sectional view of the sleeve of the present invention.

DESCRIPTION OF THE PREFERRED EMBODIMENT

With reference now to the drawings, and in particular to FIGS. 1 through 5 thereof, a new prosthesis suspension sleeve embodying the principles and concepts of the present invention and generally designated by the reference numeral 10 will be described.

More specifically, the sleeve 10 is shown in FIG. 4 and is preferably formed of resiliently stretchable non-compressive material such as urethane or polyurethane. The sleeve 10 further is shown including a first reinforced end portion 12. The first reinforced end portion 12 preferably includes an integral fabric weave which provides for circumferential stretchability or elasticity. Alternatively, the material composition may be such that the same stretchability is effected. The circumferential stretchability allows for elasticity about the thigh and further allows for proper blood flow therethrough. The fabric weave additionally provides for added strength at the first end portion 12 and prevents tearing of the sleeve 10. The integral weave does not increase the compression about the thigh.

A second reinforced end portion 20 is shown disposed opposite the first reinforced end portion 12 and is of smaller diameter than the first reinforced end portion 12. The second reinforced end portion 20 preferably includes an integral weave which provides for limited circumferential stretchability or elasticity and which additionally prevents tearing of the sleeve 10. Alternatively, the material composition may be such that the same stretchability is effected. The integral weave does not increase the compression of the urethane material. In use the second reinforced end portion 20 "locks" on the tibial section 34 of the prosthesis 30 and provides a means by which the sleeve 10 remains in position during use.

A reinforced intermediate portion 16 is shown having a generally truncated conical shape and being disposed intermediate the first and second reinforced end portions 12 and 20. The reinforced intermediate portion 16 is further shown disposed between first and second non-compressive portions 14 and 18. The reinforced intermediate portion 16 preferably includes an integral weave which provides for both circumferential and axial stretchability or elasticity while at the same time not increasing the compression of the urethane material. Alternatively, the material composition may be such that the same stretchability is effected. As shown in FIGS. 2 and 3, a typical below the knee prosthesis, 30 includes a socket 32 having a pair of "ears" 34 which extend medially and laterally of the knee and provide for openings for the patella as well as the posterior aspect of the knee. In use the reinforced intermediate portion 16 is disposed adjacent and in covering relationship to the "ears" and as such is capable of withstanding abrasive pressures exerted upon the sleeve 10.

With reference to FIG. 5, the reinforced intermediate portion 16 is shown including inner portion 17. The inner portion 17 includes a means by which the contour of the inner portion 17 can be seen by the user such as by coloring the inner portion 17 to ensure proper placement of the reinforced intermediate portion 16 over the top edge of the prosthesis socket 32.

First and second non-compressive portions 14 and 18 are shown disposed intermediate the reinforced intermediate portion 16 and the first reinforced end portion 12 and the second reinforced end portion 20 respectively. First and second non-compressive portions 14 and 18 are formed of the same resiliently stretchable non-compressive material such as urethane or polyurethane. First non-compressive portion 14 is sized and configured for adhesion to the thigh while the second non-compressive portion 18 is sized and configured for adhesion to the prosthesis 30. As is well known in the art, urethane provides for excellent adhesion and the interface between the first non-compressive portion 14 and the thigh and the second non-compressive portion 18 and the prosthesis 30 provides for suction suspension of the prosthesis 30 from the thigh. Additionally, the urethane material has excellent memory which enables the non-compressive portions 14 and 18 in particular to return to their original shapes without applying compressive forces after stretching.

To achieve the preflexed shaped of the sleeve 10, the first and second non-compressive portions 14 and 18 preferably have a truncated conical shape. First non-compressive portion 14 preferably has a longer anterior portion while the second non-compressive portion 18 preferably has a longer posterior portion. In this manner, the first non-compressive portion 14, the reinforced intermediate portion 16, and the second non-compressive portion 18 provide for an angled transition between the first reinforced end portion 12 and the second reinforced end portion 20, the end portions 12 and 20 preferably having a generally rectangular cross sectional profile. The preflexed shape provides for no constriction or binding of the knee during flexion of the knee to a point past 90° (sitting position)

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A prosthesis sleeve having generally tubular first and second end portions wherein said prosthesis sleeve comprises:

a first reinforced end portion being fully circumferentially stretchable;

an opposed second reinforced end portion of limited circumferential stretchability;

an intermediate reinforced portion being circumferentially and axially stretchable, said intermediate portion disposed intermediate the first and second reinforced end portions;

a first non-compressive portion disposed between the first reinforced end portion and the intermediate reinforced portion, said first non-compressive portion having an elongated anterior portion which achieves the preflexed configuration of the sleeve;

a second non-compressive portion disposed between the second reinforced end portion and the intermediate reinforced portion, said second non-compressive portion having an elongated posterior portion which achieves the preflexed configuration of the sleeve; and each of said first and second non-compressive portions being free of reinforcement and consisting of a flexible material having the physical property of non-compressive suction adhesion to the surface of the skin and prosthesis surfaces and being selected from the group consisting of urethane and polyurethane.

2. The prosthesis suspension sleeve of claim 1 wherein the first reinforced end portion further comprises an integral fabric weave, the integral fabric weave providing for circumferential elasticity and mechanical strength.

3. The prosthesis suspension sleeve of claim 1 wherein the second reinforced end portion further comprises an integral fabric weave, the integral fabric weave providing for limited circumferential elasticity and mechanical strength.

4. The prosthesis suspension sleeve of claim 1 wherein the intermediate reinforced portion further comprises an integral fabric weave, the integral fabric weave providing for circumferential and axial elasticity and mechanical strength.

5. The prosthesis suspension sleeve of claim 1 wherein the sleeve has a truncated conical configuration, the first reinforced end portion being of smaller diameter than the second reinforced end portion.

6. The prosthesis suspension sleeve of claim 1 wherein the sleeve has a preflexed portion coincident with the first non-compressive portion, the reinforced intermediate portion, and the second non-compressive portion.

7. The prosthesis suspension sleeve of claim 1 wherein the reinforced intermediate portion further comprises an inner portion, the inner portion further comprising a means for identifying a contour thereof.

8. A flexible prosthesis suspension sleeve having generally tubular first and second end portions and being configured for attaching a below the knee prosthesis to the limb of a person having a below the knee amputation, said prosthesis suspension sleeve comprising;

a first reinforced end portion being fully circumferentially stretchable;

an opposed second reinforced end portion of limited circumferential stretchability;

an intermediate reinforced portion being circumferentially and axially stretchable, said intermediate portion disposed intermediate the first and second reinforced end portions;

a first non-compressive portion disposed between the first reinforced end portion and the intermediate reinforced portion, said first non-compressive portion having an elongated anterior portion which achieves the preflexed configuration of the sleeve;

a second non-compressive portion disposed between the second reinforced end portion and the intermediate reinforced portion, said second non-compressive portion having an elongated posterior portion which achieves the preflexed configuration of the sleeve;

wherein the first non-compressive portion sectionally adheres to the limb and wherein the second non-compressive portion suctionally adheres to the prosthesis, and each of said first and second non-compressive portions being free of reinforcement and consisting of a flexible material having the physical property of non-compressive suction adhesion to the skin and prosthesis surfaces and being selected from the group consisting of urethane and polyurethane.

9. The flexible prosthesis suspension sleeve of claim 8 wherein the first reinforced end portion further comprises a means for providing for circumferential elasticity and mechanical strength.

10. The flexible prosthesis suspension sleeve of claim 8 wherein the second reinforced end portion further comprises a means for providing for limited circumferential elasticity and for mechanical strength.

11. The flexible prosthesis suspension sleeve of claim 8 wherein the intermediate reinforced portion further comprises a means for providing for circumferential and axial elasticity and for mechanical strength.

* * * * *